United States Patent [19]

Odagiri et al.

[11] Patent Number: 5,228,331
[45] Date of Patent: Jul. 20, 1993

[54] VISCOMETER

[75] Inventors: Tsutomu Odagiri, Chiba; Shinsuke Miura, Tokyo, both of Japan

[73] Assignee: Yamaichi Electric Co., Inc., Tokyo, Japan

[21] Appl. No.: 798,562

[22] Filed: Nov. 26, 1991

[30] Foreign Application Priority Data

Nov. 29, 1990 [JP] Japan .................. 2-333687

[51] Int. Cl.⁵ ............................................. G01N 11/16
[52] U.S. Cl. ................................................. 73/54.410
[58] Field of Search .................. 73/54.41, 54.24, 54.27

[56] References Cited

U.S. PATENT DOCUMENTS 2,707,391 5/1955 McSkimin .......................... 73/54.24
4,005,599 2/1977 Schlatter et al. ................... 73/54.27

FOREIGN PATENT DOCUMENTS 63-273041 11/1988 Japan ................................. 73/54.41
526806 8/1976 U.S.S.R. ............................. 73/54.41

Primary Examiner—Hezron E. Williams
Assistant Examiner—Joseph W. Roskos
Attorney, Agent, or Firm—Wenderoth, Lind & Ponack

[57] ABSTRACT

A viscometer has a hollow torsion bar to be dipped into a liquid, the viscosity of which is to be measured, a probe constituted by a massive hollow body mounted on the distal end of the hollow torsion bar, a vibrator mounted in the hollow body for producing vibrations in a circular direction around the axis of the torsion bar, a vibration detecting sensor mounted in the hollow body for detecting vibrations of the vibrator, a wiring pipe within the hollow torsion bar and spaced from the interior surface thereof and having conducting wires therein extending to the vibrator and to the sensor and adapted to be connected to an external vibrator driving circuit and an external vibration sensing circuit.

3 Claims, 2 Drawing Sheets

VISCOMETER

BACKGROUND OF THE INVENTION

1. Field of the Invention

This invention relates to a viscometer including a probe to be dipped into a liquid the viscosity of which is to be measured (hereinafter referred to as "measured liquid"), and a vibrator formed of a piezoelectric element and built into the probe.

2. Brief Description of the Prior Art

A viscometer disclosed in Japanese Patent Application No. Sho 62-107389 comprises a torsion bar; a probe to be dipped into a measured liquid and mounted on a distal end of the torsion bar; and a circular direction vibrator, a detector and a massive body all mounted on the other end of the torsion bar extending outside the measured liquid, circular direction vibrations being transmitted to the probe through the torsion bar.

According to the prior art, a case accommodating therein the vibrator and the massive body can turn out to be one of several disturbance factors which makes it difficult to correctly transmit vibrations of the vibrator to the probe. Moreover, the prior art device is difficult to make compact. Furthermore, although the prior art device has no problem when it is used for measuring viscosity of a sample measured liquid, it is not good when used for constantly measuring viscosity of a continuously flowing liquid.

SUMMARY OF THE INVENTION

It is therefore an object of the present invention to provide a viscometer capable of constantly measuring a continuously flowing liquid.

Another object of the present invention is to provide a viscometer which is compact in size.

A further object of the present invention is to provide a viscometer which can be protected from disturbance factors.

A still further object of the present invention is to provide a viscometer in which a satisfactory watertightness can be maintained during a measuring procedure.

A yet further object of the present invention is to provide a viscometer in which the probe itself serves as a massive body and at the same time, it accommodates therein a vibrator and a detecting sensor.

An additional important object of the present invention is to provide a sensitive and highly reliable viscometer in which vibrations of its vibrator can correctly be transmitted to its hollow torsion bar.

In order to achieve the above objects, there is essentially provided a viscometer comprising a probe serving as a massive body, a circular direction vibrator integrally accommodated within said probe, a hollow torsion bar to be dipped into the measured liquid, said torsion bar being provided with said probe mounted on a distal end portion thereof, and a wiring pipe inserted into the axial center of said torsion bar in such a manner as to be spaced apart from said torsion bar and adapted to provide a conduct for a conducting wire extending to a vibrator, etc. A detecting sensor may be accommodated within said probe together with said vibrator. Also, a wiring board adapted to connect the conducting wire in said wiring pipe to said vibrator may be disposed within said probe.

Since the present invention is constituted as described above, the probe accommodating therein the vibrator is dipped into a measured liquid through the hanging pipe of a double tubular structure which is formed of the hollow torsion bar and the wiring pipe, and the vibrator, while vibrating within the probe in the measured liquid together with the probe as mentioned above, causes the hollow torsion bar to be torsion-vibrated. The vibrator is connected to an external driving circuit through the wiring pipe which is inserted into the axial center of the torsion bar in such a manner as to be spaced apart from the torsion bar, and an electric voltage is applied thereto. The output of the detecting sensor built in the probe can be connected to an external viscosity measuring circuit through the wiring pipe.

Also, by mounting the basal end of the torsion bar, either directly or indirectly, on the pipe, etc. for permitting the measured liquid to continuously flow therethrough, viscosity of the measured liquid can be measured constantly.

Still other objects and advantages of the present invention will become readily apparent to those skilled in the art from the following detailed description, wherein only the preferred embodiment of the invention is shown and described, simply by way of illustration of the best mode of carrying out the present invention. As will be realized, the invention is capable of other and different embodiments, and its several details are capable of other and different embodiments, and its several details are capable of modifications in various obvious respects all without departing from the invention. Accordingly, the drawings and description are to be regarded as illustrative in nature, and not as restrictive.

DETAILED DESCRIPTION OF THE EMBODIMENT

A vibrator 1 for producing vibrations in a circular direction and a detecting sensor 2 use a bimorph element, respectively, which is formed of a piezoelectric element and a metal plate.

A hollow massive body is formed using a circular housing, which is circular in plan view. This hollow massive body serves as a probe 3 which is to be dipped into a measured liquid. The vibrator 1 and the detecting sensor 2 are accommodated within and integrally connected to the probe 3.

A distal end of a torsion bar 4 which acts as a resonant member and which is formed of a hollow pipe is inserted into the center of the probe 3 such that the torsion bar 4 is integrally connected to the probe 3. The vibrator 1 and the detecting sensor 2 are mounted on the inserted end of the hollow torsion bar 4. The vibrator 1 is in two parts spaced by 180 degrees about the hollow torsion bar 4 and extending radially therefrom. The detecting sensor 2 is likewise in two parts spaced by 180 degrees about the hollow torsion bar 4 and extending radially therefrom. The vibrator 1 and the detecting sensor 2 are arranged in a mutually perpendicular relation to each other.

Figure 3:
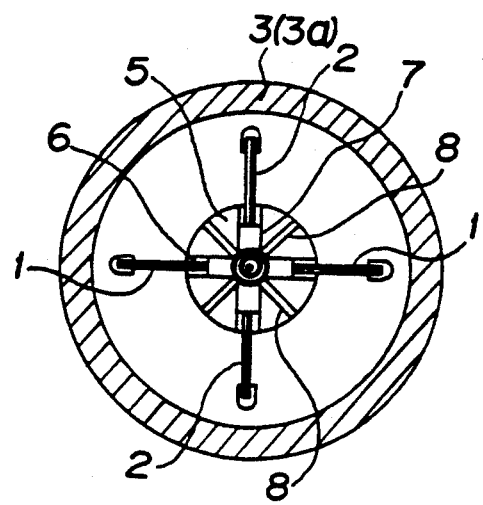
FIG. 3 is a sectional view taken on line A—A of FIG. 1, showing a vibrator and detecting sensor mounting portion.

As means for mounting the vibrator 1 and the detecting sensor 2 on the end portion of the hollow torsion bar 4, a circular holder 5 having two pairs of diametrically extending mounting grooves 6, 7 perpendicular to each other are integrally provided at the center of the probe 3 as shown in FIG. 3, the distal end portion of the torsion bar 4 being integrally mounted on the center of the holder 5, the end portion of the vibrator 1 being inserted into and integrally fixed, by adhesive or the like, in one pair 6 of the mutually perpendicular mounting grooves which are spaced by 180 degrees, the end portion of the detecting sensor 2 being inserted into and integrally fixed, by adhesive or the like, in the other pair 7 of mounting grooves which are spaced by 180 degrees, both the vibrator 1 and sensor 2 extending in the radial directions from the torsion bar 4.

The holder 5 is provided with blocking grooves 8 each extending in a radial direction between the mounting grooves 6 and 7 in order to prevent interference between the vibrator 1 and the detecting sensor 2.

The probe 3 constituted by the hollow massive body is comprised of a cup-shaped housing body 3a and a cover 3b. The probe 3 is formed into a water-tight hollow structure by, for example, threadedly engaging the cover 3b to the housing body 3a. The distal end of the torsion bar 4 is inserted into the center of the cover 3b and fixed water-tightly to the cover 3b. For example, the holder 5 is formed by providing a boss projecting inwardly toward the center of the probe 3 from the cover 3b and having the mounting grooves 6, 7 in the boss.

A wiring pipe 9 is inserted axially into the interior of the hollow torsion bar 4 formed on a hollow pipe. The wiring pipe 9 is spaced apart from the hollow torsion bar 4 by an annular space 10 to thereby form a double tubular structure. The distal end of the wiring pipe 9 projects into the probe 3 formed of a hollow massive body from the distal end of the hollow torsion bar 4. The projected end of the wiring pipe 9 is provided with a circuit board 11 attached thereto. Within the wiring pipe 9, a conducting cable 12 having conducting wire for interconnecting the vibrator 1 and an external driving circuit as well as a conducting wire for interconnecting the detecting sensor 2 and an external measuring circuit is inserted. One end of the conducting wire 12 for the vibrator is connected to the wiring board 11 and further to the vibrator 1 by lead wire 13 and the detecting sensor 2 is connected to the detecting sensor conducting wire by means of a lead wire 13 through the wiring board 11. By virtue of the foregoing arrangement, interference between the wiring system and the vibrator 1 and detecting sensor 2 can be prevented.

Figure 1:
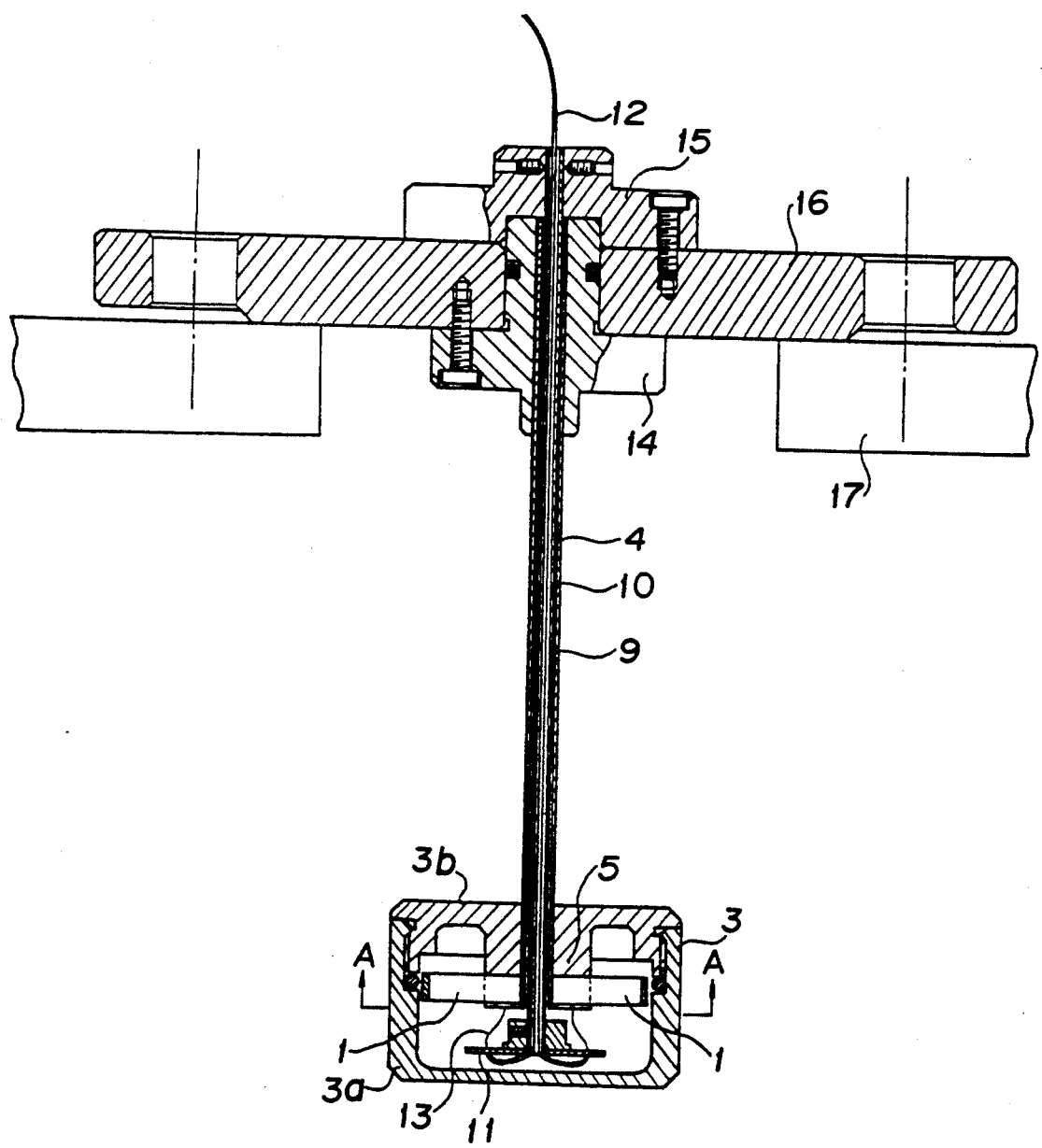
FIG. 1 is a sectional view of a viscometer showing one embodiment of the present invention.

As is shown in FIG. 1, a flange 16 serving as a massive mounting body is integrally mounted on the basal end of the hollow torsion bar 4 through tightening members 14, 15. The flange 16 is mounted over an opening in a pipe 17 for conducting a measured liquid therethrough, so that the probe 3 can be dipped into the measured liquid.

The basal end of the hollow torsion bar is fixed to one of the fastening members 14, 15 so as to be integral with the flange 16. The basal end of the wiring pipe 9 projects from the basal end of the hollow torsion bar 4 and is fixed to the other fastening member. Owing to the foregoing arrangement, the wiring pipe 9 is hung on the axis of the torsion bar but spaced apart from the hollow torsion bar 4. The flange 16 is sandwiched between and fastened by the fastening members 14, 15 in order to integrally assemble the various component elements.

Figure 2:
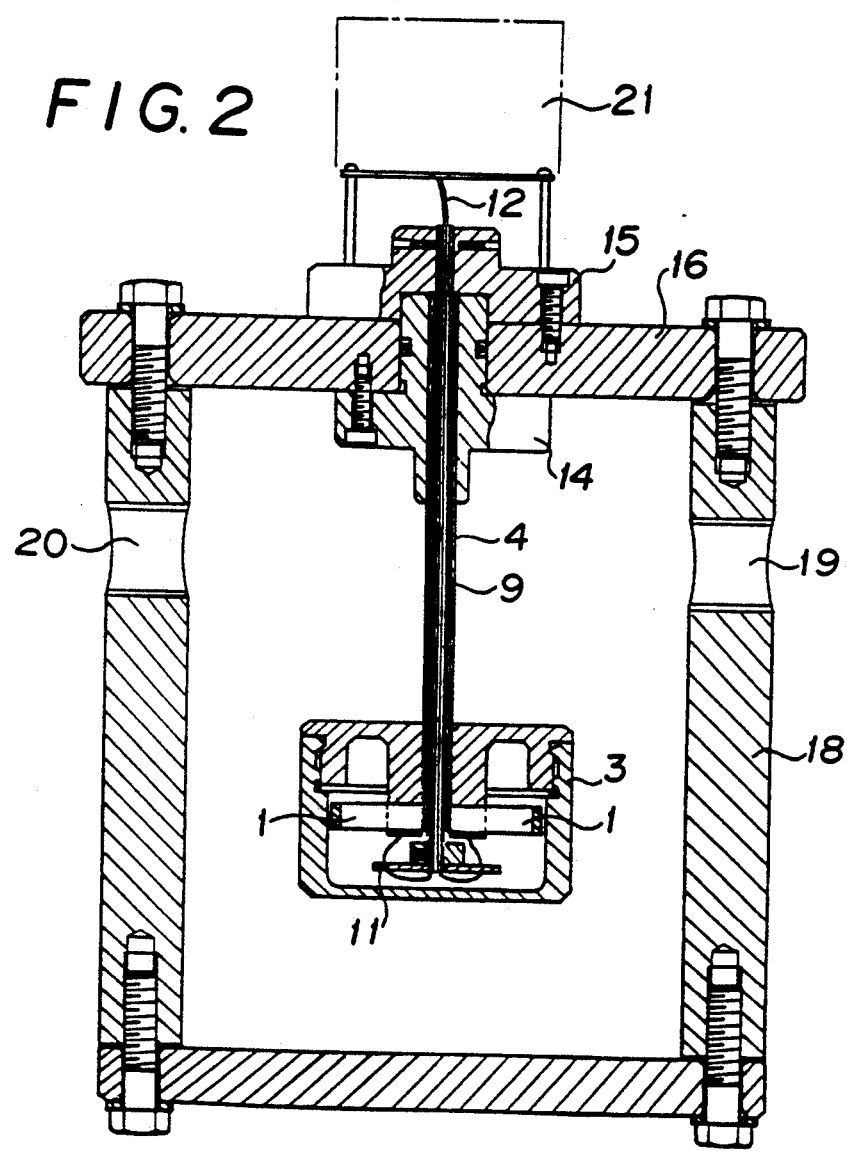
FIG. 2 is a sectional view showing another embodiment of the present invention.

In FIG. 2, the flange 16 serves as a cover, and a detecting container 18 is provided in such a manner as to be integral with the flange 16. The probe 3, which is hung by means of the hollow torsion bar 4, is accommodated within the detecting container 18. The container 18 is provided with a liquid inlet port 19 formed in one side wall thereof and with a liquid outlet port 20 formed in the other side wall. Viscosity is detected by introducing a measured liquid into the container 18 from the inlet port 19 and guiding the same out through the outlet port 20. In this embodiment, the flow velocity of the measured liquid is reduced within the container 18, so that the detection of viscosity can be stably carried out by virtue of the probe 3.

The numeral 21 denotes a circuit device having a driving circuit for the vibrator 1 disposed on an upper part, for example, the flange 16 of the detecting container 18, and further having a measuring circuit connected to the detecting sensor 2. The respective circuits disposed within the circuit device 21 are connected to the various elements within the probe by means of the conducting wires extending through the wiring pipe 9.

According to the present invention, a vibrator, or a vibrator and a detector are built in a probe to be dipped into a liquid, and the probe accommodating therein the vibrator and detector is dipped into a measured liquid through a hollow torsion bar. The vibrator and detector are connected to a driving circuit and a measuring circuit through a wiring pipe inserted into the hollow torsion bar. Accordingly, the viscometer as a whole can be simplified in structure and can be assembled into a compact size. Especially, it has a structure suitable for mounting on a pipe for passing liquid therethrough used in factories, etc. The invention can be favorably applied to a viscometer for constantly measuring viscosity of a flowing liquid.

Furthermore, according to a viscometer of the present invention, the vibrator and the detecting sensor can be protected from various external factors, and the water-tightness between the vibrator and sensor and the wiring portion can be maintained favorably during a measuring procedure.

Moreover, the probe itself serves as a massive body, and it also accommodates therein a vibrator and a detecting sensor for direct connection. And the probe accommodating those elements is hung by means of a hollow torsion bar. Accordingly, vibrations of the vibrator can be transmitted to the hollow torsion bar by effectively obviating the disturbance factor, and a correct measurement of viscosity can be made by the detecting sensor. In this way, there can be provided a sensitive and highly reliable viscometer.

In this disclosure, there is shown and described only the preferred embodiments of the invention, but, as aforementioned, it is to be understood that the invention is capable of use in various other combinations and environment and is capable of changes or modifications within the scope of the inventive concept as expressed herein.

What is claimed is:

1. A viscometer, comprising:
   a hollow torsion bar to be dipped into a liquid, the viscosity of which is to be measured;
   a probe constituted by a massive hollow body, said probe being mounted on a distal end portion of said hollow torsion bar;

a vibrator mounted in said hollow body for producing vibrations in a circular direction around a longitudinal axis of said torsion bar;

a vibration detecting sensor within said hollow body and spaced from said vibrator for detecting vibrations of said vibrator;

a wiring pipe mounted within said torsion bar along said longitudinal axis thereof and spaced from the interior of said torsion bar; and conducting wires in said wiring pipe extending through said wiring pipe to said vibrator and to said sensor and adapted to be connected to an external vibrator driving circuit and an external vibration measuring circuit.

2. A viscometer as claimed in claim 1 further comprising a circuit board mounted within said hollow body to which said conducting wires are connected and in turn connected to said vibrator and said sensor, respectively.

3. A viscometer as claimed in claim 1 further comprising a massive mounting body on which a base end of said hollow torsion bar and a base end of said wiring pipe are separately mounted, whereby said torsion bar can twist around said wiring pipe independently thereof.

* * * * *